United States Patent [19]

Doellein

[11] Patent Number: 5,399,781
[45] Date of Patent: Mar. 21, 1995

[54] METHOD OF PRODUCING $Ph_3C[B(C_6F_5)_4]$

[75] Inventor: Guenther Doellein, Hanover, Germany

[73] Assignee: Solvay Deutschland GmbH, Hanover, Germany

[21] Appl. No.: 134,613

[22] Filed: Oct. 12, 1993

[30] Foreign Application Priority Data

Oct. 17, 1992 [DE] Germany .......... 4235092.1

[51] Int. Cl.$^6$ .......... C07F 5/02
[52] U.S. Cl. .......... 568/6
[58] Field of Search .......... 568/6

[56] References Cited

PUBLICATIONS

Chien et al., "Isospecific Polymerization of Propylene . . .", *J. Am. Chem. Soc.*, vol. 113, pp. 8570–8571 (1991).

Primary Examiner—Johann Richter
Assistant Examiner—John Peabody
Attorney, Agent, or Firm—Evenson, McKeown, Edwards & Lenahan

[57] ABSTRACT

A method for producing $Ph_3C[B(C_6F_5)_4]$ in an improved yield by reacting $LiB(C_6F_5)_4$, which has not been isolated between production and use, with $Ph_3CCl$ preferably in a molar ratio of $LiB(C_6F_5)_4$ to $Ph_3CCl$ of 1:(1±0.05), and preferably in the presence of a hydrocarbon solvent such as an aliphatic hydrocarbon containing from 5 to 8 carbon atoms, to give a $Ph_3C[B(C_6F_5)_4]$ product; optionally evaporating the hydrocarbon solvent; extracting the resulting $Ph_3C[B(C_6F_5)_4]$ product; separating insoluble LiCl, and isolating the product. The product may be isolated, for example, by freeing it of solvent, thereafter dissolving the product in toluene to form a toluene solution, introducing the toluene solution into a hydrocarbon solvent to form crystals of the product, and recovering the crystals. In the method, the $LiB(C_6F_5)_4$ is used in the form of a hydrocarbon preparation, preferably a reaction mixture obtained in the synthesis of $LiB(C_6F_5)_4$, the concentration of may be adjusted by concentrating or diluting as needed to obtain a preferred $LiB(C_6F_5)_4$ concentration of from 20 to 300 grams/liter.

10 Claims, No Drawings

METHOD OF PRODUCING PH3C[B(C6F5)4]

BACKGROUND OF THE INVENTION

The invention relates to a method for producing Ph$_3$C[B(C$_6$F$_5$)$_4$]. The "cation" of the compound [Et-(Ind)$_2$Zr(CH$_3$)]$^+$B(C$_6$F$_5$)$_4$$^-$(Ind=Indenyl) is a catalyst for the isospecific polymerization of propylene. The catalytic compound is produced in accordance with the following reaction equation:

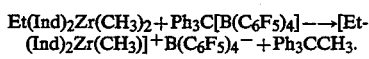

Et(Ind)$_2$Zr(CH$_3$)$_2$+Ph$_3$C[B(C$_6$F$_5$)$_4$]→[Et-(Ind)$_2$Zr(CH$_3$)]$^+$B(C$_6$F$_5$)$_4$$^-$+Ph$_3$CCH$_3$.

The Ph$_3$C[B(C$_6$F$_5$)$_4$] which is required as an intermediate product, and its production are described by J. C. W. Chien, Woei-Min Tsai and M. D. Rausch in *J. Am. Chem. Soc.* 113 (1991), pages 8570 and 8571. In the method described therein, LiB(C$_6$F$_5$)$_4$ is mixed under an argon atmosphere with triphenylmethyl chloride (Ph$_3$CCl) in 200 ml dry n-hexane and is refluxed overnight. The yellow solid was dissolved in dichloromethane and lithium chloride was removed by filtration. The product was then recrystallized from dichloromethane/hexane, and was obtained in the form of orange-colored crystals. The yield is given as 64%.

SUMMARY OF THE INVENTION

It is an object of the present invention to provide a method for producing triphenylcarbenium-tetrakis(pentafluorophenyl)borate which gives this compound in a higher yield.

This and other objects of the invention are achieved in accordance with the present invention by providing a method for producing Ph$_3$C[B(C$_6$F$_5$)$_4$] comprising the steps of:
  reacting LiB(C$_6$F$_5$)$_4$ with Ph$_3$CCl to give a Ph$_3$C[B(C$_6$F$_5$)$_4$] product;
  extracting the resulting Ph$_3$C[B(C$_6$F$_5$)$_4$] product;
  separating insoluble LiCl and
  isolating the product;
wherein said LiB(C$_6$F$_5$)$_4$ is used in the form of a hydrocarbon preparation with the proviso that the LiB(C$_6$F$_5$)$_4$ has not been isolated between production thereof and use thereof.

DETAILED DESCRIPTION OF PREFERRED EMBODIMENTS

The method according to the invention for producing Ph$_3$C[B(C$_6$F$_5$)$_4$] by reacting LiB(C$_6$F$_5$)$_4$ with Ph$_3$CCl, extraction of the resulting product and separation of insoluble LiCl and isolation of the product, is characterized in that the LiB(C$_6$F$_5$)$_4$ is used in the form of a hydrocarbon preparation with the proviso that the LiB(C$_6$F$_5$)$_4$ used has not been isolated from the time of its production until its use. It is therefore important to the invention that the LiB(C$_6$F$_5$)$_4$ which upon its production occurs in the form of a solvent-containing reaction mixture is not completely freed of solvent until it is used in the reaction with Ph$_3$CCl. It is quite possible to perform an exchange of solvents or to dilute or concentrate the reaction mixture which occurs upon production. The hydrocarbon preparation preferably contains LiB(C$_6$F$_5$)$_4$ in a concentration of 20 to 300 grams/liter. It is particularly preferred to carry out the production of LiB(C$_6$F$_5$)$_4$, preferably from butyl-lithium and pentafluorobromobenzene and boron trichloride, in a hydrocarbon solvent, and to carry out the further processing thereof by reaction with Ph$_3$CCl in the manner of a "one-pot" reaction. In this case, the BCl$_3$ may be used in pure form or as a solution in a hydrocarbon solvent.

Preferably the hydrocarbon solvent is an aliphatic hydrocarbon with 5 to 8 carbon atoms or a mixture of such hydrocarbons. Since butyl-lithium is usually used as a solution in n-hexane, the hydrocarbon solvent then accordingly contains n-hexane as a constituent. It is particularly preferred to add n-pentane or n-hexane as a further solvent.

It is preferred to use the lithium-boron compound and Ph$_3$CCl in a molar ratio of 1:(1±0.05).

The reaction between the lithium-boron compound and Ph$_3$CCl may be completed in a subsequent reaction phase. In this case, the reaction mixture is preferably maintained for up to 20 hours, particularly 8 to 20 hours, at ambient temperature or at elevated temperature, e..g. between 30 and 100° C. (when using n-pentane and n-hexane, for example at about 50° C.). The resulting solid contains the product and LiCl Preferably the solvents are then evaporated, and a suitable solvent for the desired product, preferably dichloromethane, is added. The insoluble LiCl is filtered out and subsequently washed, until the filter residue is colorless. The filtrate is concentrated, and a little hydrocarbon solvent, preferably n-hexane, is added thereto. The product occurs in the form of orange-colored crystals, which are filtered out and dried. Alternatively and preferably, the solvent, e.g. the dichloromethane, is largely or completely evaporated, the residue is dissolved in an aromatic solvent, particularly toluene, and the solvent is allowed to run into the hydrocarbon solvent, preferably n-hexane. The resulting crystals are then filtered out and dried.

The method according to the invention gives the desired product in a high yield and with high purity. It can be used with great success for producing a catalyst for polymerizing ethylene or propylene.

The following examples are intended to illustrate the invention in further detail, without restricting its scope.

EXAMPLE 1

Production of Ph$_3$C[B(C$_6$F$_5$)$_4$].

32.1 g (0.13 mole) bromopentafluorobenzene in 100 ml n-pentane were placed in a 500-ml three-necked flask equipped with a thermometer, stirrer and dropping funnel. The flask contents were cooled to −78° C. Under inert gas, 79.3 ml of a solution of lithium-n-butyl (0.13 mole; 1.6M in n-hexane) was added thereto in drops such that the temperature of the reaction mixture did not exceed −70° C. The resulting white suspension was then stirred for 20 minutes at −78° C. Then 3.81 g (2.82 ml; 0.0325 mole) boron trichloride were added with a syringe. The cooling means was removed, and the mixture was thereafter stirred for 2 hours at room temperature. Then 9.1 g (0.0325 mole) of trityl chloride (Ph$_3$CCl) were added to the reaction mixture. The suspension then turned yellow. The reaction was completed by a 16-hour subsequent reaction phase at 50° C., in which the reaction mixture boiled. The solvents pentane and hexane were distilled off, approximately 300 ml dichloromethane were added to the yellow solid and were filtered off from the insoluble solid. The filter residue (predominantly LiCl) was washed until it became colorless. The filtrate was concentrated, and a little n-hexane was added thereto. When allowed to stand, orange-colored crystals formed, which were filtered out and dried.

Yield: 24.4 g (81.3% of theoretical) Elemental analysis:

| | |
|---|---|
| $B_{calc.}$: 1.17% | $B_{found}$: 1.24% |
| $C_{calc.}$: 55.99% | $C_{found}$: 55.70% |

Example 2

Modified method for producing $Ph_3C[B(C_6F_5)_4]$.

The procedure of Example 1 was repeated. After the addition of the trityl chloride, the reaction mixture was allowed to stand for 16 hours at room temperature in order to complete the reaction. After the yellow solid had been extracted with dichloromethane and the filter residue had been washed with dichloromethane, the filtrates were combined and the dichloromethane was evaporated. The remaining residue was dissolved in toluene. When the solution was added to n-hexane, orange-colored crystals were produced immediately, which were filtered out and dried. The yield for this energy-saving and time-saving method corresponded to the yield achieved in Example 1.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for producing $Ph_3C[B(C_6F_5)_4]$ comprising the steps of:
    reacting $LiB(C_6F_5)_4$ with $Ph_3CCl$ to give a $Ph_3C[B(C_6F_5)_4]$ product;
    extracting the resulting $Ph_3C[B(C_6F_5)_4]$ product;
    separating insoluble LiCl, and
    isolating the product;
    wherein said $LiB(C_6F_5)_4$ is used in the form of a hydrocarbon preparation with the proviso that the $LiB(C_6F_5)_4$ has not been isolated between production thereof and use thereof.

2. A method according to claim 1, wherein said hydrocarbon preparation is a reaction mixture obtained in the synthesis of $LiB(C_6F_5)_4$.

3. A method according to claim 1, wherein said hydrocarbon preparation is produced by concentrating a reaction mixture obtained in the synthesis of $LiB(C_6F_5)_4$.

4. A method according to claim 1, wherein said hydrocarbon preparation is produced by diluting a reaction mixture obtained in the synthesis of $LiB(C_6F_5)_4$.

5. A method according to claim 1, wherein said hydrocarbon preparation contains $LiB(C_6F_5)_4$ in a concentration of from 20 to 300 grams/liter.

6. A method according to claim 1, wherein said reacting step is carried out in the presence of a hydrocarbon solvent, further comprising the step of evaporating the hydrocarbon solvent prior to said extracting step.

7. A method according to claim 6, wherein said hydrocarbon solvent is selected from the group consisting of aliphatic hydrocarbons containing from 5 to 8 carbon atoms and mixtures thereof.

8. A method according to claim 1, wherein $LiB(C_6F_5)_4$ and $Ph_3CCl$ are used in said reacting step a molar ratio of $1:(1\pm0.05)$.

9. A method according to claim 1, wherein said isolating step is carried out by freeing the product of solvent; thereafter dissolving the product in toluene to form a toluene solution; introducing the toluene solution into a hydrocarbon solvent, whereby crystals of the product are formed; and recovering said crystals.

10. A method according to claim 9, wherein said hydrocarbon solvent is n-hexane.

* * * * *